United States Patent [19]

Prins

[11] 4,243,387
[45] Jan. 6, 1981

[54] ADJUSTABLE ORTHODONTIC BRACKET

[76] Inventor: Steven P. Prins, 531 Tomahawk Trail, Woodstock, Ga. 30188

[21] Appl. No.: 30,101

[22] Filed: Apr. 16, 1979

[51] Int. Cl.³ .............................................. A61C 3/00
[52] U.S. Cl. ..................................................... 433/16
[58] Field of Search ......................................... 433/16

[56] References Cited

U.S. PATENT DOCUMENTS

| 2,379,011 | 6/1945 | Laskin | 433/16 |
| 3,203,098 | 8/1965 | Petraitis | 433/23 |
| 3,423,833 | 1/1969 | Pearlman | 433/16 |
| 3,721,005 | 3/1973 | Cohen | 433/16 |
| 4,139,945 | 2/1979 | DiGiulio | 433/16 |

Primary Examiner—Gene Mancene
Assistant Examiner—John J. Wilson
Attorney, Agent, or Firm—James B. Middleton

[57] ABSTRACT

An adjustable bracket for use in orthodontic appliances. The bracket can be fixed to a band to surround a tooth, or to a wire mesh to be cemented directly to a tooth. The bracket has a base to be carried by the tooth, and a movable member to which wires are attached, and a retainer to fix the movable member to the base. In the preferred embodiment, the base and the movable member have spherical surfaces so that motion of the movable member can dispose the bracket at any desired angle in any plane for the desired torque, and in all embodiments the movable member is rotatable about the retainer through 360 degrees and can be set at any desired angle.

4 Claims, 9 Drawing Figures

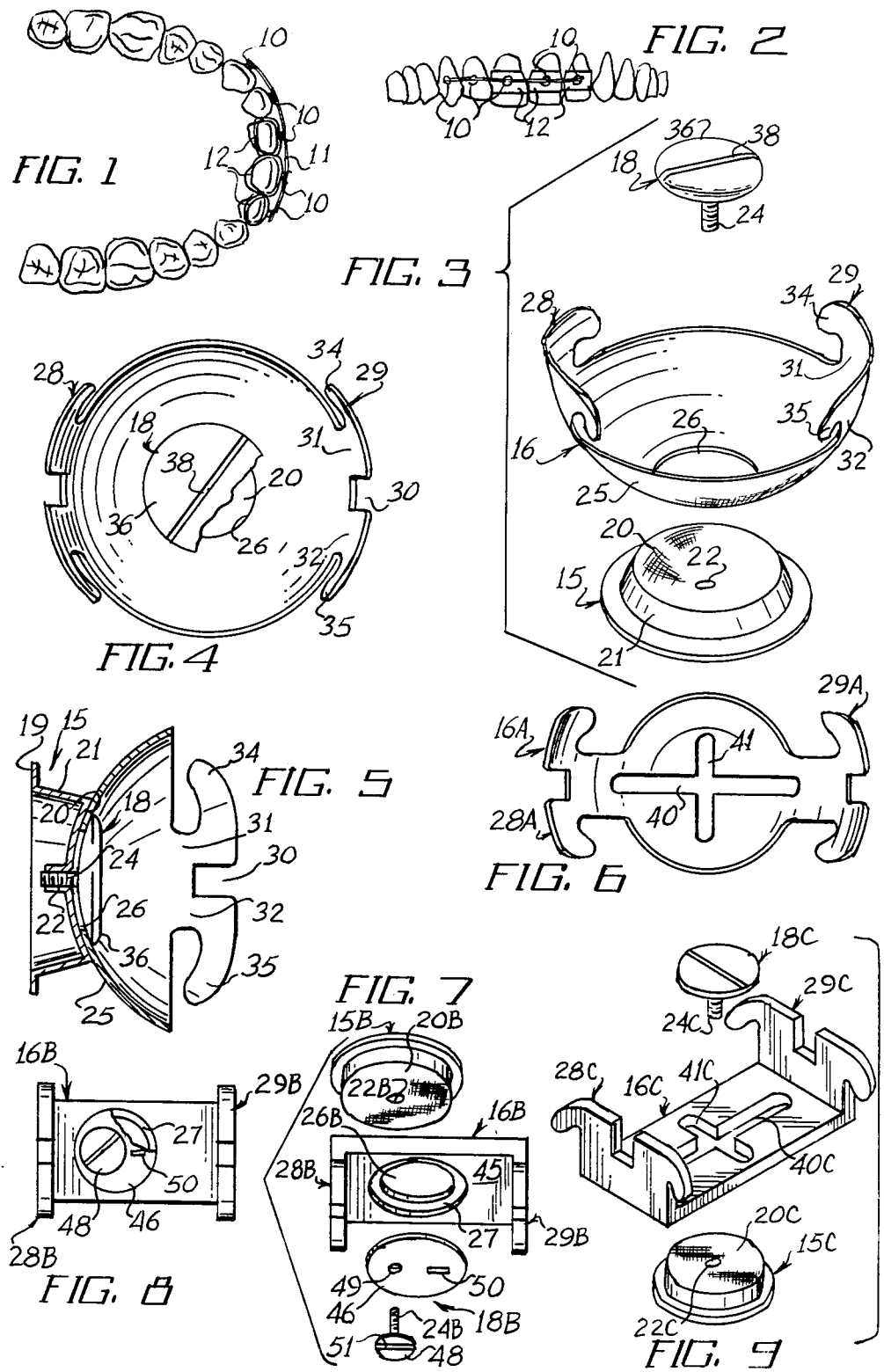

ADJUSTABLE ORTHODONTIC BRACKET

This invention relates generally to orthodontic appliances, and is more specifically concerned with an adjustable bracket for use in conjunction with orthodontic appliances.

When an orthodontist is to straighten a person's teeth, the orthodontist must design an appliance which is generally to be carried by the person's teeth. The appliance has means to exert forces on the crooked, or non-aligned, teeth to cause the teeth to be moved and to be brought into alignment. The presently conventional orthodontic appliances are constructed by attaching a bracket to each tooth to be moved, then fixing a wire to each bracket to exert the desired forces on the tooth. The brackets are most commonly fixed to a band which encircles the tooth, though sometimes the bracket is fixed to a tooth by attaching a wire mesh to the back side of the bracket, the mesh then being cemented to the tooth. In either case, the result is that a bracket is fixed with respect to a given tooth, the bracket being adapted to receive wires to bring about desired motion of the tooth.

In the past, the brackets have been fixed to the tooth, or to a band which is fixed to a tooth, and the wires had to be bent or otherwise manipulated in order to exert a desired force on a tooth. One improvement in this prior art arrangement has been the design of a bracket having the wire-receiving notch angularly disposed with respect to the horizontal axis of the bracket so that a straight wire can be placed into the bracket and the wire will exert the desired force on the tooth.

Using the brackets having an angularly disposed notch, the orthodontist can select the appropriate bracket to exert the appropriate force on the tooth; however, the orthodontist must retain in stock a great variety of brackets having different angles, and having a notch designed to go on the left side of the mouth, and a separate group of brackets having notches designed to go on the right side of the mouth. An extremely large inventory is therefore required for an orthodontist to be prepared for the variety of conditions he meets in everyday practice. Additionally, the angled notch in the bracket is arranged to exert forces about only one axis, i.e., the angled notch in the bracket is arranged so that a torque is exerted generally in the plane of the anterior surface of the tooth. However, if the orthodontist needs to exert a torque on the tooth tending to rotate the tooth about its centerline, i.e., axially of the tooth, a small wedge, generally known as a Steiner wedge, is placed between the wire and the band. In addition to the simple fact of the requirement of an additional piece in order to provide this axial rotation of the tooth, the Steiner wedge is quite difficult to insert properly since it must be put into place after the appliance is fixed to the patient's tooth.

There have been previous efforts to provide an adjustable bracket for othodontic appliances, but none has met with commercial success. The prior art adjustable brackets have generally been rather complex in their structure, either utilizing an arrangement that is very difficult to adjust, or using a plurality of pins, hinge joints and the like. Many of the prior art adjustable brackets have been adjustable only for the first use, the construction being such that the bracket is permanently fixed in place once the angle is set as desired.

The present invention overcomes the above-mentioned and other difficulties with the prior art brackets by providing an orthodontic bracket which is adjustable to provide any desired degree of torque. In the preferred embodiment of the invention, the bracket made in accordance with the present invention is universally adjustable so that the orthodontist can utilize a single bracket and make appropriate adjustments to exert a torque in the plane of the anterior surface of a tooth, and in a plane transverse to such plane of the tooth, or axially of the tooth, or any combination of these. The bracket is designed to be cemented directly to the tooth by means of a wire mesh attached to the base of the bracket, or to be fixed to a band that surrounds the tooth. In the case of the use of a band, it will be understood that, due to the universal adjustability of the bracket, the orthodontist can consider only the size of the band to determine which tooth will receive the band, because the bracket can be adjusted for the left or the right side of the mouth, and can be arranged to exert any desired torque in that position. Other embodiments of the invention provide less adjustability but would be desirable in particular circumstances. One embodiment of the invention includes eccentric means whereby the brackets can be effectively moved with respect to the band after the band is in place on a tooth. Additionally, the bracket of the present invention is very simple in construction and is easy to adjust as desired. After the bracket is set, the same bracket can be readjusted at will to follow the changing needs of the patient. It will therefore be seen that the present invention provides an orthodontic bracket adjustable for very general use so that the orthodontist can adjust a single bracket to exert any desired amount of torque, and can readjust the bracket as treatment progresses. This also allows the orthodontist to have a much smaller inventory of brackets on hand without in any way diminishing the range of treatment available.

These and other features and advantages of the present invention will become apparent from consideration of the following specification when taken in conjunction with the accompanying drawings in which:

FIG. 1 is a bottom plan view of a set of teeth having an orthodontic appliance fixed thereto, the appliance being constructed using brackets made in accordance with the present invention;

FIG. 2 is a front elevational view of the teeth and the orthodontic appliance shown in FIG. 1;

FIG. 3 is an exploded perspective view showing a universally adjustable bracket made in accordance with the preferred form of the present invention;

FIG. 4 is a top plan view, partially broken away, of the bracket shown in FIG. 3;

FIG. 5 is a cross-sectional view taken generally along the line 5—5 in FIG. 4;

FIG. 6 is a top plan view of a modified form of force-receiving member to be used in the bracket shown in FIGS. 3 through 5;

FIG. 7 is an exploded perspective view of a modified form of bracket made in accordance with the present invention;

FIG. 8 is a top plan view of the bracket shown in FIG. 7 of the drawings; and,

FIG. 9 is an exploded perspective view of another modified form of the present invention.

Referring now more particularly to the drawings, and to those embodiments of the invention here chosen by way of illustration, FIGS. 1 and 2 show a plurality of brackets 10 fixed with respect to teeth, and having a wire 11 extending through the various brackets 10. For purposes of illustration, it will be seen that three of the teeth are provided with orthodontic bands 12, and the brackets 10 are fixed to the bands 12. Though such an arrangement would probably not be used in practice, for purposes of illustration two of the teeth have the brackets 10 illustrated as being attached to the teeth without an orthodontic band. Those skilled in the art will realize that a conventional wire mesh would be welded or otherwise fixed to the bracket to allow the brackets to be cemented directly to the teeth.

Looking at FIG. 2 of the drawing, it will be realized that the wire 11 tends to extend along a horizontal line; therefore, if the bracket 10 is provided with a slot angularly disposed with respect to the horizontal line, the wire will exert a torque on the tooth having such bracket affixed thereto. Furthermore, the greater the angle, the greater the torque that will be exerted by the wire, and the direction of the force will depend on the direction of the angle of the bracket.

In FIG. 1 of the drawing, it will be seen that, if the bracket 10 is adjusted so that one side protrudes farther from the anterior surface of the tooth than the other, the wire 11 will exert an axial torque on the tooth, that is to say a torque tending to rotate the tooth about its longitudinal center line.

Looking now at FIG. 3 of the drawing for a more detailed description of the particular bracket of the present invention, it will be seen that the device illustrated in FIG. 3 of the drawing includes generally a base member 15 adapted to receive a force receiving member 16, and a retaining member 18 for retaining the force receiving member 16 in place on the base 15.

Referring to FIGS. 3, 4 and 5, it will be seen that the base 15 includes a generally flat rear surface 19 which would be attached to a band, such as the bands 12, or to a wire mesh in the event the bracket is to be cemented to a tooth. The base 15 has a front, concave, surface 20, and a solid skirt 21 extends from the rear surface 19 to the concave forward surface 20. The concave surface 20 is here indicated as being knurled, and the reason for the knurling will be understood hereinafter.

Generally centrally of the concave surface 20 there is a threaded hole 22 to receive the threaded shank 24 of the retainer 18 as will be discussed more fully hereinafter.

The force receiving member 16 is designed to have wires such as the wire 11 fixed thereto, and also to receive elastics, springs, and other devices which provide forces to be transmitted to a tooth. The force receiving member 16 is therefore receivable on the base 15, and includes a convex surface 25 shaped to mate with the concave surface 20. The convex surface 25 is here shown as including knurling also to be complementary with the surface 20. As will become more fully understood hereinafter, it is preferable that the concave surface 20 and the convex surface 25 be spherical, though other shapes may be used to achieve different forms of adjustability.

The force receiving member 16 is somewhat bowl-shaped, but has a large opening 26 in the bottom thereof. The side walls of the bowl-shaped member have, formed integrally therewith, two pairs of ears generally designated at 28 and 29. Those skilled in the art will realize that orthodontic brackets are conventionally formed with notches for receiving wires and hooks for receiving elastics. In the present invention, these notches and hooks are formed by the ears 28 and 29 as best shown in FIGS. 4 and 5 of the drawings. Here it will be seen that there is a rectangular notch 30 defined between the two ears 31 and 32; and, each of the ears 31 and 32 is formed with hook members 34 and 35 respectively, facing away from the notch 30. It will thus be seen that a wire can be received within the notch 30, and a ligature can be engaged with the ears 31 and 32 to secure the wire. The hook members 34 and 35 are also appropriately placed to receive elastics if required. It should be observed that the notch 30 is rectangular so that a square wire or other non-round wire can be placed into notch 30, and the wire can be axially twisted to exert a rotational force on the bracket.

Though only the pair of ears 29 has been discussed in detail, it will be understood that the pair of ears 28 is formed as a precise mirror image of the pair of ears 29 and no further description is deemed necessary.

Looking now at the retainer 18 in FIGS. 3, 4 and 5, it will be seen that the retainer 18 includes the shank 24 which can pass through the opening 26 in the force receiving member 16 and threadedly engage the hole 22 in the base 15. The retainer 18 also includes an enlarged head 36 having a slot 38 for receipt of a conventional screwdriver blade. As is best shown in FIGS. 4 and 5 of the drawings, the head 36 of the retainer 18 is of considerably larger diameter than the opening 26 in the force receiving member 16, and the bottom surface of the head 36 is shaped complementarily to the inside of the bowl-like structure of the force receiving member 16.

From the foregoing description, those skilled in the art should now understand the operation of this embodiment of the present invention. The rear surface 19 of the base 15 would be fixed to a band 12 or to a piece of mesh so that the bracket can be appropriately fixed to a tooth. The force receiving member 16 is received by the concave surface 20, and the retainer 18 is placed with its shank 24 passing through the opening 26 and into the threaded opening 22. With the retainer 18 rotated to disengage the head 36 from the inside of the force receiving member 16, the force receiving member 16 can be moved to any extent in any direction until the edge of the opening 26 engages the shank 24 of the retainer 18. As a result, the force receiving member 16 can be angled in any direction. Also, it will be obvious that the force receiving member 16 can be rotated through 360 degrees about the axis of the shank 24.

When the force receiving member 16 is adjusted as desired, an ordinary screwdriver can be used to place in the slot 38 and rotate the retainer 18, causing the threaded shank 24 to thread into the threaded hole 22 until the retainer firmly holds the force receiving member 16 against the base 15. Since the convex surface 25 and the concave surface 20 are knurled, only reasonable tightening of the retainer 18 will be necessary to prevent inadvertent slippage. Also, it will be understood that knurling is only one means of holding the surfaces with respect to each other, and other means such as roughening the surfaces by blasting them with shot or other conventional techniques may also be used.

In the mass manufacture of the device in accordance with the present invention, it will be understood that the base 15 and force receiving member 16 might well be formed by die stamping. In this event, the dies can be provided with an appropriate roughened surface, and the roughened surface of the dies will be transmitted to the pieces stamped by the dies so that no further treatment will be required.

With this embodiment of the present invention, it will now be seen that the force receiving member 16 can be adjusted so that the notches 30 are angularly disposed with respect to the center line of the bracket, and this angle can be in either direction. Similarly, the force receiving member 16 can be moved with respect to the base so that the pair of ears 28 is farther forward than the pair of ears 29, or vice versa, which would give the effect of placing a wedge under the wire 11. Furthermore, the force receiving member 16 can be moved to achieve a combination of the two above described motions so that the orthodontist has complete control over the forces exerted on a tooth simply by adjusting the force receiving member 16 with respect to the base 15.

It will be understood that orthodontic bands are tapered as is a tooth so that a band cannot be turned upside down. Nevertheless, if the bracket of the present invention is fixed to a given band, the band can be used on either side of the patient's mouth and the bracket can be adjusted for the desired angle.

Attention is next directed to FIG. 6 of the drawings which shows a modified form of a force receiving member designated as 16A. The force receiving member 16A is quite similar to the member 16, and is shaped to be received by the concave surface 20. The member 16A is formed to be generally spherical in shape and includes two pairs of ears 28A and 29A comparable to the pairs of ears 28 and 29 shown in FIGS. 3, 4 and 5.

The main body of the force receiving member 16A has been reduced as much as possible; and, instead of having a large circular opening 26 as in the member 16, the member 16A includes crossed slots 40 and 41. It will thus be seen that the member 16A is used similarly to the member 16, the shank 24 of the retainer 18 passing through the slots 40 and/or 41 and into the threaded hole 22. The head 36 of the retainer 18 will press against the upper surface of the member 16A to hold it in position against the base 15. The member 16A would be somewhat less expensive to produce since it would require less material, and the only real sacrifice is the only slightly less versatile motion of the member 16A.

Because of the slot 40, it will be seen that the force receiving member 16A can be moved to cause one of the pairs of ears 28A or 29A to extend forward to give the effect of having a wedge between the wire and the tooth. Because of the slot 41, the force receiving member 16A can also be adjusted to angle the notch with respect to the axis of the bracket. With either of these two angles, the member 16A can be rotated about the shank 24 through 360 degrees to provide any desired angle with respect to the horizontal.

Attention is next directed to FIGS. 7 and 8 of the drawings which disclose another embodiment of the adjustable bracket of the present invention. It will here be seen that the device includes a base member 15B adapted to receive a force receiving member 16B, the force receiving member 16B being held to the base 15B by means of a retainer 18B.

The base 15B includes a front, flat surface 20B having a central, threaded hole 22B for receipt of a threaded shank 24B. It will be understood that the base 15B is adapted to be fixed either to a mesh for being cemented directly to a tooth, or to a band as is conventional. The surface 20B of the base 15B is knurled or otherwise roughened to assist in preventing inadvertent motion of the force receiving member 16B with respect to the base 15B.

The force receiving member 16B has an opening 26B, the hole 26B being counterbored as at 27. The body 45 of the force receiving member 16B is generally flat, and has two pairs of ears 28B and 29B, one pair at each end of the body 45.

The retainer 18B is in two pieces in the present embodiment of the invention, the retainer comprising a positioning disk 46 and a screw 48. It will be seen that the retainer disk 46 includes a hole 49 only slightly larger than the shank 24B of the screw 48, the hole 49 being displaced from the center of the disk 46. There is also a slot 50 to allow rotation of the disk 46.

From the foregoing description, it should now be understood that the base 15B can be fixed to an orthodontic band or the like, and the force receiving member 16B can be placed on the surface 20B of the base 15B. The retainer disk 46 would then be placed within the counterbore 27 with the hole 49 directly aligned with the hole 22B. The shank 24B of the screw 48 can then be passed through the hole 49 and into the threaded hole 22B. Appropriate rotation of the screw 48, utilizing its slot 51, will cause the screw 48 to seat against the disk 46 and hold the force receiving member 16B in place. When the screw 48 is somewhat loosened, it will be understood that the force receiving member 16B can be rotated about the disk 46. It is important to note that the rotation of the force receiving member 16B will be about the center of the disk 46 rather than about the shank 24B, but the angle of the notches can be any angle desired by the orthodontist.

Though the embodiment of the invention shown in FIGS. 7 and 8 of the drawings cannot achieve the wedging effect or the angling of the notches along the axis of a wire, the device shown in FIGS. 7 and 8 of the drawings has the advantage of being movable with respect to a tooth without changing any of the angular adjustments of the bracket. This is achieved because of the eccentricity of the mount through the retaining disk 46. It will be seen that, since the shank 24B is displaced from the center of the disk 46, if the screw 48 is slightly loosened, and the disk 46 is rotated while holding the force receiving member 16B in its desired horizontal position, the entire force receiving member 16B will be displaced with respect to the base 15B. This added dimension of adjustability can sometimes be extremely helpful to the orthodontist.

The embodiment of the invention shown in FIG. 9 of the drawing provides about the same function as the device of FIGS. 7 and 8. In the embodiment of the invention, the force receiving member 16C is similar to the member 16B, but crossed slots 40C and 41C are provided. A retainer means 18C includes a head 36C having a threaded shank 24C extending therefrom. The base 15C, then, is similar to the base 15B and includes a threaded hole 22C to receive the shank 24C.

Thus, it will be seen that the embodiment of the invention shown in FIG. 9 provides for rotation of the force receiving member 16C through 360 degrees, and additionally allows the member 16C to be shifted to either side, or up and down due to the slots 40C and 41C.

It should now be understood by those skilled in the art that the adjustable orthodontic bracket of the present invention provides an extremely simple bracket that can be adjusted as needed by the orthodontist. In the course of treatment, if the patient requires less torque, a bracket would normally have to be removed, along with the band carrying the bracket, and an entirely new band and bracket would have to be cemented in place on the tooth, and the entire device rewired. With the bracket of the present invention, the retaining member 18 can be loosened, and the force receiving member 16 can be appropriately adjusted and retightened without the trauma or expense of installing a totally new band and bracket. Furthermore, the force receiving member and retaining member should be easily usable a plurality of different times so that an orthodontist may keep a large number of bands having bases 15 attached thereto, and the force receiving members and retaining members can be reused, thereby reducing the cost to the orthodontist. The brackets are adjustable in all respects so that a supply of variously angled brackets would not be required, and the same bracket can be used on the left side or the right side of the mouth, again reducing the necessary inventory of the orthodontist.

It will of course be understood by those skilled in the art that the particular embodiment of the present invention here shown are by way of illustration only, and are meant to be in no way restrictive; therefore, numerous changes and modifications may be made, and the full use of equivalents resorted to, without departing from the spirit or scope of the invention as defined in the appended claims.

I claim:

1. An orthodontic appliance comprising at least one bracket carried by a tooth, and a wire fixed to said bracket for exerting a force on said bracket so that the force is exerted on the tooth, characterized in that said bracket includes a base fixed with respect to said tooth, a force receiving member selectively receivable on said base and movable with respect thereto, said force receiving member defining means for receiving said wire, retainer means for selectively fixing said force receiving member with respect to said base, said force receiving member defining an opening therein, said retainer means including a shank receivable through said opening and engageable with said base, said force receiving member being selectively rotatable about said retainer means for changing the angular position of said means for receiving said wire, and further characterized in that said base includes a concave surface for receiving said force receiving member, said force receiving member includes a convex surface complementary to said concave surface, and said opening is generally central of said force receiving member, the arrangement being such that said means for receiving said wire can be angularly disposed with respect to said base by motion of said force receiving member with respect to said base.

2. An orthodontic appliance as claimed in claim 1, and further characterized in that said convex surface of said force receiving member is a spherical surface, and said concave surface of said base is a spherical surface having the same radius, and said opening is a generally circular opening so that said force receiving member can be moved in any direction with respect to said base.

3. An orthodontic appliance as claimed in claim 2, characterized in that said base defines a threaded hole centrally thereof, said shank of said retainer means comprises a threaded member threadedly receivable by said threaded hole, and a head having a diameter greater than the diameter of said opening.

4. An orthodontic appliance comprising at least one bracket carried by a tooth, and a wire fixed to said bracket for exerting a force on said bracket so that the force is exerted on the tooth, characterized in that said bracket includes a base fixed with respect to said tooth, a force receiving member selectively receivable on said base and movable with respect thereto, said force receiving member defining means for receiving said wire, retainer means for selectively fixing said force receiving member with respect to said base, said force receiving member defining an opening therein, said retainer means including a shank receivable through said opening and engageable with said base, said force receiving member being selectively rotatable about said retainer means for changing the angular position of said means for receiving said wire, and further characterized in that said retainer means includes a retainer disk having a hole therein for receiving said shank said hole being off-set from the center of said retainer disk, said opening in said force receiving member having a counterbore concentric with said opening, and said retainer disk being rotatably receivable with said counterbore, a head carried by said shank larger than said hole in said retainer disk, and means for rotating said retainer disk with respect to said force receiving member.

* * * * *